United States Patent [19]

Moore

[11] 4,432,823
[45] Feb. 21, 1984

[54] METHOD AND APPARATUS FOR MANUFACTURING ELASTIC LEG DISPOSABLE DIAPERS

[75] Inventor: William J. Moore, Winnebago County, Wis.

[73] Assignee: Kimberly Clark Corporation, Neenah, Wis.

[21] Appl. No.: 278,753

[22] Filed: Jun. 29, 1981

[51] Int. Cl.³ ............................................. B32B 31/08
[52] U.S. Cl. ...................................... 156/164; 83/13; 83/701; 156/229; 156/270; 156/291; 156/495; 156/522; 156/554
[58] Field of Search .......................... 83/13, 54, 701; 156/164, 229, 269, 270, 291, 522, 554, 495, 516

[56] References Cited
U.S. PATENT DOCUMENTS 4,081,301 3/1978 Buell ................................. 156/522
4,227,952 10/1980 Sabee ............................... 156/270
4,360,398 11/1982 Sabee ............................... 156/164

*Primary Examiner*—Jerome W. Massie
*Attorney, Agent, or Firm*—Richard C. Ruppin

[57] ABSTRACT

A method and apparatus for elasticizing the leg areas of disposable diapers is disclosed. Portions of a continuously moving elastic ribbon are attached to a continuously moving web at spaced apart locations along the length of the web corresponding to the leg areas of a finished diapers. The web is moved over at least one arcuate surface and the portions of the ribbon that are not attached to the web are drawn through a slot in the surface so that the unattached ribbon portions separate from the web and travel a shorter path than the web. While the unattached portions of the ribbon are passing through the slot, they are clamped intermediate their ends by clamping means. While the unattached ribbon portions are held clamped, they are cut at their ends by cutting means.

12 Claims, 13 Drawing Figures

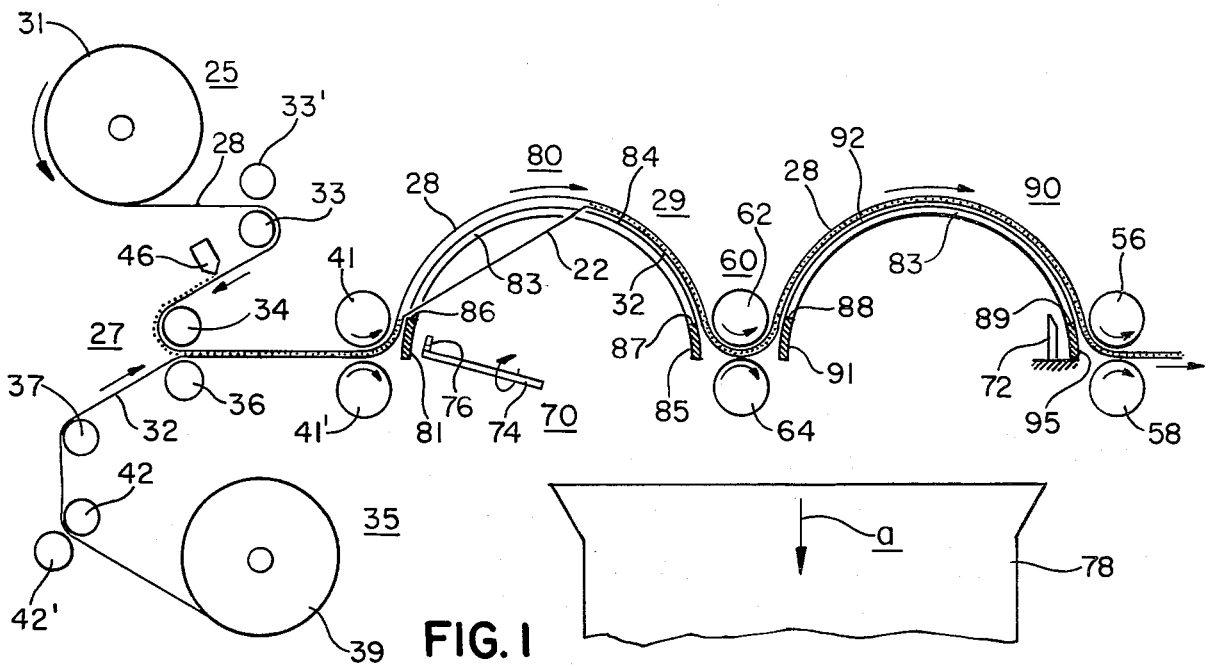
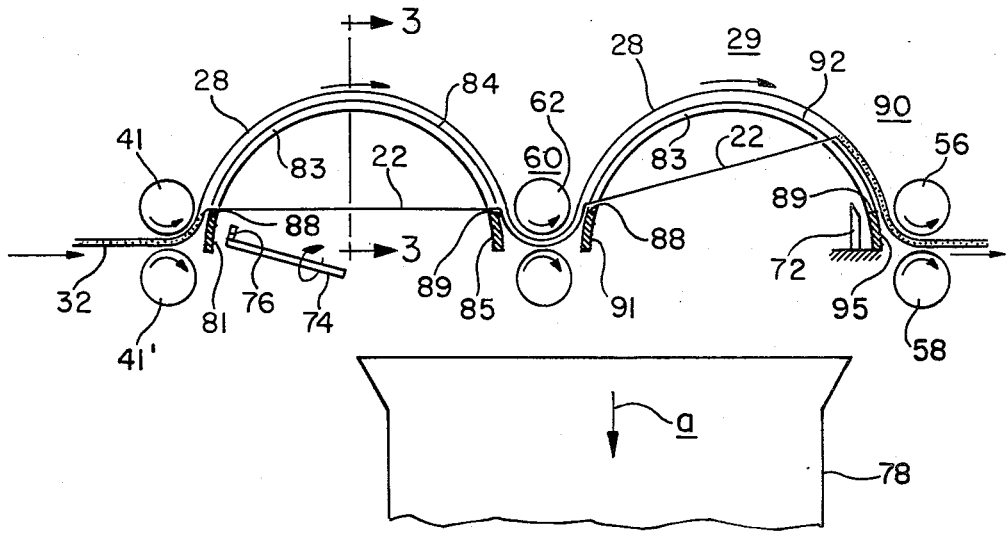
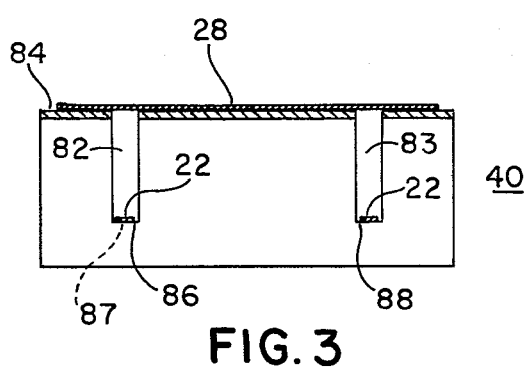
FIG. 1
FIG. 2
FIG. 3

20# METHOD AND APPARATUS FOR MANUFACTURING ELASTIC LEG DISPOSABLE DIAPERS

FIELD OF THE INVENTION

This invention relates to an apparatus and method for elasticizing only the leg areas of disposable diapers and in particular to an apparatus and method for removing elastic from other than the lega areas of a disposable diaper where it is not desired to have elastic. The subject matter of this application is related to that of application Ser. No. 278,619, by W. C. Sigl, assigned to the same assignee as that of the instant invention.

BACKGROUND OF THE INVENTION

Due to the improved fit and fluid sealing properties provided by leg elasticization, manufacturers of disposable diapers have, in recent years, developed various methods and apparatus for attaching elastic strips to the leg areas of the diapers. Because of the high speed, continuous nature of diaper manufacturing methods, virtually all of the commercially practicable processes have utilized a continuous elastic ribbon affixed to the diaper in the leg areas and subsequently cut either prior to or as a part of the severing of the continuous web into separate diapers. Typical of these processes and apparatus is that disclosed in U.S. Pat. No. 4,081,301 to Buell. This patent discloses adhering of the continuous elastic ribbon only in discrete, intermittent areas corresponding to the leg areas in a finished diaper. The ribbin and the diaper are then simultaneously cut at the waist of the diaper when the continuous web is cut into separate diapers. The drawback of this process is that it is inefficient from the material use aspect in that it leaves an unneeded length of elastic attached to the diaper. Another approach to handling the problem is disclosed in U.S. Pat. No. 4,227,952 to Sabee. In the method of this patent, the elastic ribbon is continuously applied to the web, however, before the attachment of the ribbon to the web, the latter is folded in the areas of the web corresponding to the waist areas of the finished diapers. Consequently, the elastic ribbon is attached to the web only in the leg areas of the finished diaper. The elastic ribbon is then severed at the points opposite the folded areas of the web and the web is then unfolded so that elastic is only in the leg areas and the waist areas contain no unneeded elastic. The problem with this method and the apparatus used in it is that they are quite complex and difficult to operate at the high speeds required for commercial usefulness.

It is a principal object of this invention to provide a method and apparatus for attaching a continuously moving elastic ribbon to a continuously moving web only in the areas of the web corresponding to the leg areas in finished diapers and removing the portions of the elastic ribbon between the attached areas in a simple and commercially practicable manner.

SUMMARY OF THE INVENTION

The objective of the invention is accomplished by providing an apparatus in which the elastic ribbon and web are continuously moved together and the ribbon attached at spaced apart locations on the web corresponding to the leg areas of the finished diaper. While the web and the elastic ribbon are moving together, the web is separated from the ribbon in the areas of the ribbon that are not attached to the web. The separating of the web from the unattached portions of the ribbon is accomplished by supporting the web on one or more surfaces which causes the web to move along a path having a longer length than the length of the path of movement of the unattached portions of the ribbon. To permit the unattached portions of the ribbon to move this shorter distance, a slot is provided in the supporting surface or surfaces through which the unattached ribbon portions pass so that separation occurs. The elastic ribbon is preferably subjected to elongating tension while being attached to the web so that, when the elastic ribbon is permitted to follow a shorter path through a slot, the unattached portion of the ribbon will relax and in fact move through the slot. While the unattached portions of the ribbon are thus separated from the web, both ends of the unattached portions of the ribbon may be cut, preferably adjacent the location of the attached portions of the ribbon. Although it is desirable to have the ribbon under tension so that its unattached portions have a greater tendency to contract and follow the shorter path through the slot, it is also necessary that the unattached portions be under tension to enable their rapid cutting. Since the cuts at both ends of the unattached ribbon portions may not occur simultaneously, a clamping means is provided to hold the unattached portions so that, after the first cut is made, tension is maintained at the end where the second cut is to be made to facilitate the making of the second cut. After the completion of both cuts, the ribbon may be removed.

BRIEF DESCRIPTION OF THE DRAWINGS

Further objects and advantages of the invention will appear when taken in conjunction with the accompanying drawings, in which:

FIG. 1 is a simplified side elevation view showing the web supply, elastic supply, elastic bonding, and elastic removal stations of the diaper manufacturing apparatus of the invention;

FIG. 2 is a simplified side elevation view similar to FIG. 1 showing only the elastic removal station just prior to the cutting of the elastic ribbon at its leading end;

FIG. 3 is a cross-sectional view taken along section line 3—3 of FIG. 2 and showing only the elastic removal station;

DETAILED DESCRIPTION OF THE INVENTION

Figure 12:
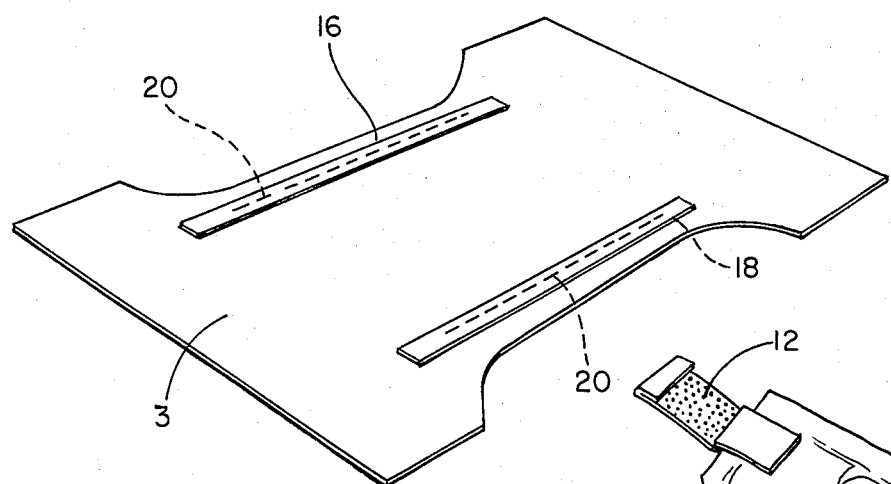
FIG. 12 is a perspective view showing the back sheet of a disposable diaper which comprises a section of the web, with elastic strips attached in the leg areas.
Figure 13:
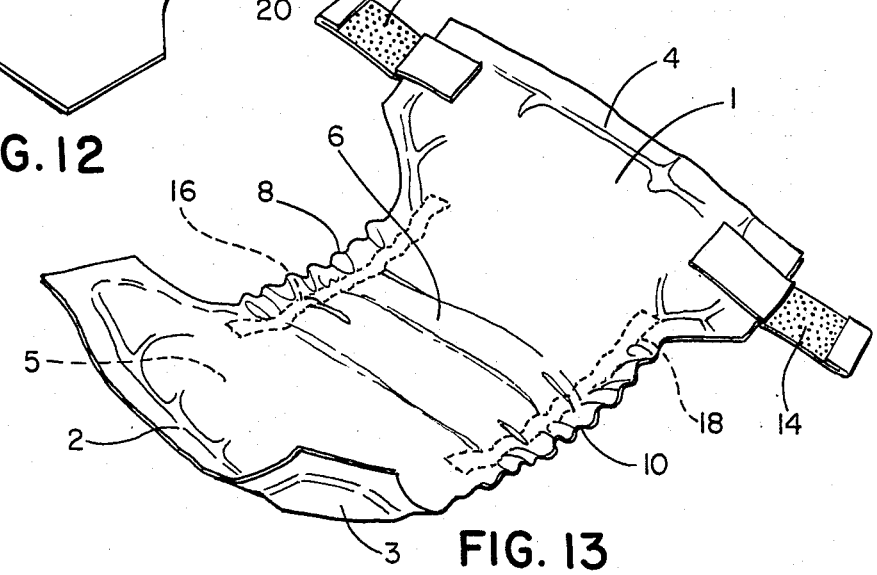
FIG. 13 is a perspective view of a finished elasticized leg disposable diaper just prior to its fitting onto a wearer.

For purposes of background, the elasticized leg disposable diaper produced by the apparatus and method of the invention will initially be discussed. Referring first to FIGS. 12 and 13, there is shown in FIG. 13 a disposable diaper having a topsheet 1, a backsheet 3, an absorbent pad 5 between the topsheet 1 and backsheet 3, a front waist area 2, a rear waist area 4, and a crotch area 6 intermediate the two waist areas. Leg areas 8 and 10 are positioned laterally of the crotch area 6 and intermediate of the waist areas 2 and 4. Waist fastening tapes 12 and 14 are bonded to the corner areas of the rear waist area 4 and are fastenable to the front waist area 2 when the diaper is fitted to a wearer to secure the diaper on the wearer. Elastic strips 16 and 18 are attached substantially parallel to the length of the diaper in the leg areas 8 and 10 respectively, as shown in FIG. 12, to elasticize the leg areas of the diaper and provide a snug fit around the legs of a wearer. In FIG. 13, the elastic strip 16 and 18 are shown in a relaxed condition in which they cause random pleating or folding of the topsheet 1 and backsheet 3.

In FIG. 12, the only diaper components shown are the backsheet 3, the elastic strips 16 and 18 and adhesive lines 20 respectively attaching the elastic strips 16 and 18 to the backsheet 3. The backsheet 3 and the elastic strips 16 and 18 are shown in an extended, flat condition in which the elastic strips 16 and 18 are stretched.

Referring now generally to FIGS. 1–5, apparatus is shown for supplying a web 28 and elastic ribbons 30 and 32, attaching the ribbons 30 and 32 to the web 28, and removing portions of the ribbons 30 and 32 which are not attached to the web 28. Apparatus for applying the absorbent pad 5, the waist fasteners 12 and 14, and the topsheet 2 are not shown or described herein inasmuch as they form no part of the present invention and may be of types that are well known in the art. Also, the apparatus and method will be described with reference to FIGS. 1–10, only with respect, in most instances, to continuous elastic ribbon 32 since the method and the operation of the apparatus is the same for both of the ribbons 30 and 32.

In FIG. 1 is shown a web supply station 25 at which the web material 28 is drawn from a supply roll 31 by feed rolls 33 and 33' and fed to the elastic attaching station 27. At the elastic ribbon supply station 35, the elastic ribbon 32 is drawn from supply roll 39 by feed rolls 42 and 42'. The elastic ribbon 32 is then passed over a tension sensing roll 37 which, through feedback means (not shown), controls the speed of the feed rolls 42 and 42' such that the elastic ribbon 32 is maintained under tension as it moves with the web 28 through the elastic attaching station 27 and the elastic removal station 29.

Figure 11:
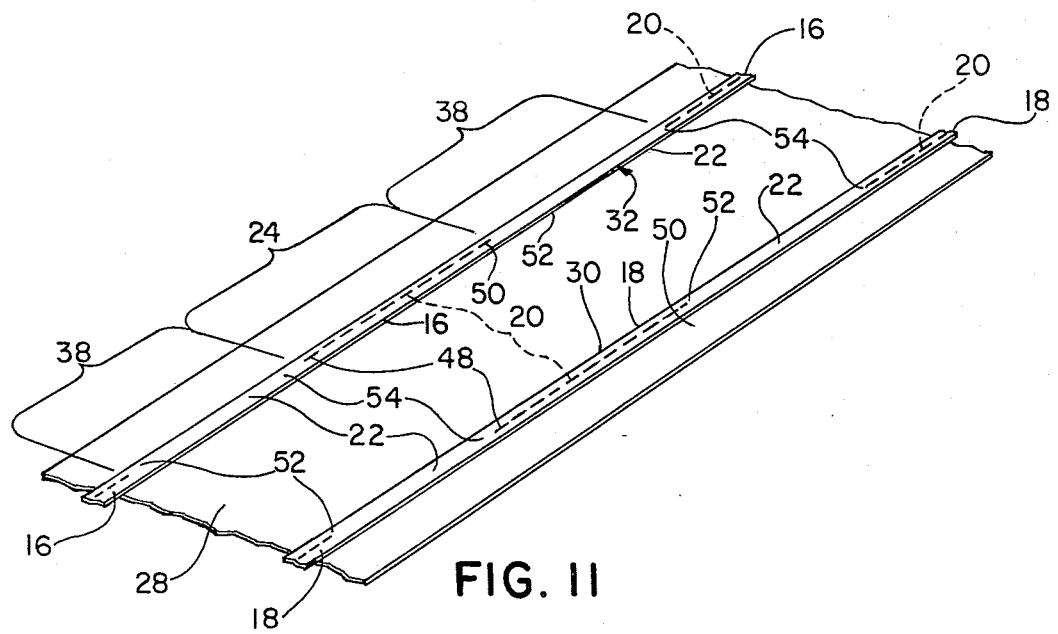
FIG. 11 is a perspective view of the web and elastic ribbons illustrating the attached and unattached portions of the ribbon.

At the elastic attaching station 27, adhesive nozzles 46 apply adhesive lines 20 to the web 28 along paths substantially parallel to the length of the web 28 and its direction of travel (see FIG. 12). The nozzles 46 operate such that adhesive is applied to the web 28 only at spaced apart locations 24 along the length of the web 28, as illustrated in FIG. 11. The spaced apart locations 24 on the web 28 correspond to the leg areas 8 and 10 of the finished diapers. Subsequent to the application of the adhesive lines 20 to the web 28, the web 28 and the elastic ribbon 32 are moved together through a pair of nip rolls 34 and 36 which press the web 28 and the elastic ribbon 32 together to thereby attach or bond the ribbon 32 to the web 28 only along the spaced apart locations 24 to which the adhesive lines 20 have been applied. Thus, there are portions 22 of the elastic ribbon 32 along locations 38 of web 28 which are unattached to the web 28 between the attached portions or strips 16 and 18 (see FIG. 12) along locations 24 on the web 28. As is best illustrated in FIG. 11, the attached elastic portions 16 and 18 of ribbons 30 and 32 on the web 28 have ends 48 and 50 and the unattached portions 22 of ribbon 30 have ends 52 and 54.

After attachment of the elastic ribbon 32 to the web 28, the web 28 with the ribbon 32 passes between idler rolls 41, 41' as they move to elastic removal station 29. In the embodiment of the invention shown in FIGS. 1–5, the elastic removal station 29 includes a pair of web support means 80 and 90 preferably having a pre-ferably arcuate cross-sectional shape, a ribbon clamping means 60, and elastic cutting means 70. The support means 80 has ends 81 and 85 and the support means 90 has ends 91 and 95. The support means 80 and 90 respectively have arcuate shaped surfaces 84 and 92. Each arcuate support means 80 and 90 also include a slot 82 having ends 86 and 87 and a slot 83 having ends 88 and 89 as shown in FIGS. 2 and 3. The clamping means 60 comprises a pair of idler rolls 62 and 64 respectively positioned on opposite sides of the elastic ribbon 32 and web 28 so that the path of movement of the web 28 and elastic ribbon 32 passes between the rolls 62 and 64. As shown in FIG. 1, the clamping means 60 is positioned between the arcuate support means 80 and 90 adjacent their respective ends 85 and 91. The cutting means 70 includes a stationary hot knife 72 and a rotating hot knife 74 having a cutting blade 76. The stationary hot knife 72 is positioned adjacent the end 95 of arcuate support means 90 and the rotating hot knife 74 is positioned adjacent the end 86 of arcuate support means 80. The knives 72 and 74 are positioned such that they will respectively cut the leading ends 54 and the trailing ends 52 of unattached elastic portions 22 as the unattached elastic portions 22 move through the slots 82 and 83, as will be described in greater detail hereinafter. A vacuum means 78 is provided to remove the severed unattached elastic pieces 22 in the direction of the air flow as shown by the arrow after their severing by the cutting means 70. After removal of the elastic portions 22, the web 28 will have attached to it only elastic portions or strips 16 and 18. The web 28 and elastic strips 16 and 18 then exit the elastic removal station 29 through the drive rolls 56 and 58 and move toward additional stations of the diaper manufacturing apparatus. At the additional stations, other components will be added and further operations will be performed to produce a finished elasticized leg diaper.

Figure 4:
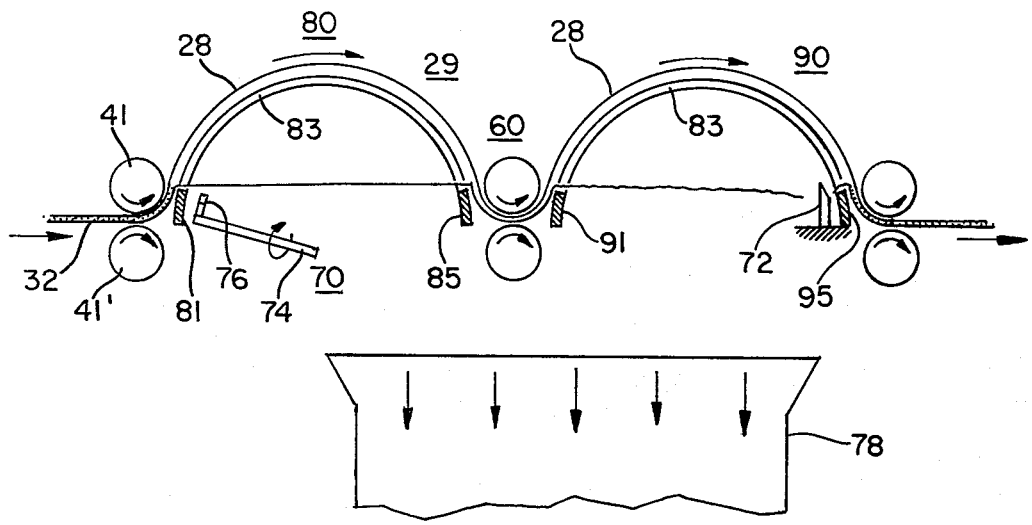
FIG. 4 is a simplified side elevation view similar to FIG. 2 showing the elastic removal station just subsequent to the cutting of the leading end of the unattached portion of the elastic ribbon and just prior to the cutting of its trailing end.
Figure 5:
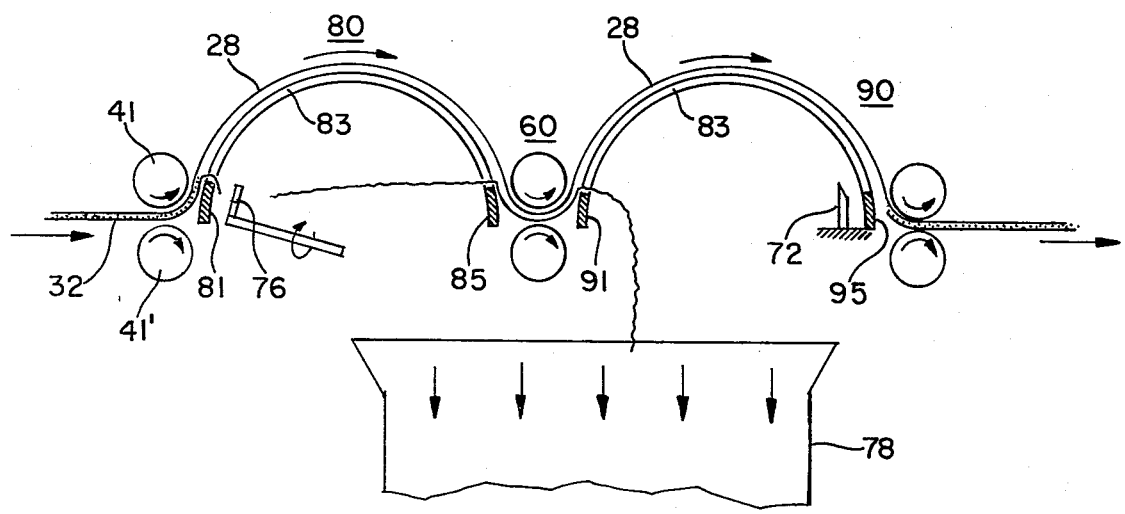
FIG. 5 is a simplified side elevation view similar to FIGS. 2 and 4 showing the elastic removal station just subsequent to the cutting of the trailing end of the unattached portion of the elastic ribbon.

Considering FIGS. 1-5 further, as the web 28 moves over the arcuate support means 80, it will follow a path along the surface 84, as shown in FIGS. 1 and 3. However, since the slot 83 is positioned in alignment with the location on the web 28 of continuous elastic ribbon 32, the unattached ribbon portions 22 of the continuous ribbon 32 are not supported by the surface 84 and are free to move through the slot 83 after the ribbon portions 22 pass the end 88 of the slot 83. The ribbon portions 22 may fall through the slot due to their own weight, however, if the ribbon 32 is stretched while being applied to the web 28, the opportunity to follow the shorter path through the slot 83, rather than along the longer path over the surface 84, will result in the elastic portions 22 relaxing from their stretched condition and thereby moving through the slot 83. As the web 28 and continuous elastic ribbon 32 continue through the elastic removal station 29, the web and ribbon pass between the rolls 62 and 64 of clamping means 60 and the web 28 then continues over the surface 92 of arcuate support means 90. However, similarly to the movement of unattached elastic portions 22 as the web 28 passed over support means 80, the unattached ribbon portions 22 of continuous ribbon 32 will pass through the slot 83 of support means 90, as shown in FIG. 2. With reference to FIG. 4, an unattached ribbon portion 22 has reached the end 89 of slot 83 and has been severed by the stationary knife 72 which it contacts at approximately the same time that it reaches the slot end 83. Meanwhile, the web 28 and an attached elastic strip 16 continue out of the elastic removal station 29 between drive rolls 56 and 58. Due to variations in the amount of stretch of the continuous ribbon 32 and/or the web 28 and variations in the timing of the apparatus related to the elastic removal station 29, the cutting of the trailing end 52 of the ribbon portion 22 may take place at a different time than the cutting of its leading end 54. Thus, in FIG. 4, the trailing end 52 of the unattached elastic portion 22 is shown just prior to being cut by the blade 76 of rotating knife 74 whereas the leading end 54 of elastic ribbon portion 22 has already been severed. The rotating knife 74 is driven by any suitable drive mechanism (not shown) which will bring the knife blade 76 into contact with the unattached ribbon portion 22 when the trailing end 52 of a ribbon portion 22 is at the slot end 86. In FIGS. 1 and 2, the cutting blade 76 is shown rotating away from the unattached ribbon portion 22 after having severed a trailing end 52 of a previous ribbon portion 22. In FIG. 4, the cutting blade 76 is shown rotating toward the ribbon end 52 just prior to severing the ribbon portion 22. In FIG. 5, the cutting blade 76 is shown just subsequent to the cutting of the ribbon end 52.

Although the unattached ribbon portions 22 relax from their stretched condition when applied to the web 28 as the ribbons 22 pass through the slots 83, some tension nevertheless does remain in the ribbon portions 22 after they have passed through the slots 83 and this tension is necessary to their rapid and effective cutting by either the stationary knife 72 or the rotating knife 74. However, if the ends 52 and 54 of the ribbon portion 22 are not cut simultaneously, the cutting of one of these ends prior to the cutting of the other cutting of one of these ends prior to the cutting of the other will result in the ribbon portion 22 relaxing entirely so that there will not be the necessary tension in the ribbon to permit the making of the second cut. The clamping means 60 is provided to maintain tension in the end 52 or 54 of a ribbon portion 22 that is cut subsequent to the cutting of the the other end. By passing the web 28 and the unattached ribbon portion 22 between the rollers 62 and 64 of the clamping means 60, the ends 52 and 54 are isolated from each other insofar as their tension condition is concerned. Thus, upon the severing of either of the ends 52 or 54, tension remains in the other end so that it also may be cut under tension. After severing of both ends 52 and 54 of the unattached ribbon portion 22, the severed ribbon portion 22 is removed by the vacuum removal means 78 from the elastic removal station 29. The beginning of the removal of the cut piece of ribbon portion 22 is shown in FIG. 5.

In FIGS. 6-10 is illustrated a second embodiment of the invention in which at an elastic removal station 94, only a single support means 100 is utilized, a clamping means 110 comprises a pair of continuous, moving belts 112 and 114, and a cutting means 130 includes a single rotating cutting blade 132. As in the embodiment illustrated in FIGS. 1-5, the idler rolls 41 and 41' act as a guide means for the feeding of the web 28 and continuous elastic ribbon 32 to the elastic removal station 94. Also similarly to the embodiment of FIGS. 1-5, the drive rolls 56 and 58 guide the removal of the web 28 and the elastic strips 16 and 18 from the elastic removal station 94 and drive the web 28 and elastic strips on to additional stations of the diaper manufacturing apparatus. The belts 112 and 114 are continuously driven by any suitable power source (not shown) through drive chains 116, 116', drive sprockets 118, 118' and 120, 120', drive rolls 122, 122' and 124, 124'. A pair of idler rolls 126, 126' guide the belts 112 and 114 so that, as the belts rotate, corresponding locations on each belt converge toward each other. Guide rolls 128, 128' and 129, 129' hold the belts in engagement with each other. The drive chains 116, 116' and all of the drive sprockets and rolls comprising part of the clamping means 110 are supported on frame members 108, 108', shown only in FIG. 6. The belts 112 and 114 are respectively driven in a clockwise and counterclockwise direction, relative to the view of FIG. 7, and converge toward each other between idler rolls 126, 126' and form a nip 121 adjacent idler rolls 128, 128'. The cutting means 130 is also supported on the frame members 108, 108' and is rotatably driven from any suitable power source (not shown).

The support means 100 has a preferably arcuate surface 102 and a slot 104 having opposite ends 106 and 107. Vacuum removal means 138 is provided for the removal of cut pieces of unattached ribbon portions 22.

Figure 6:
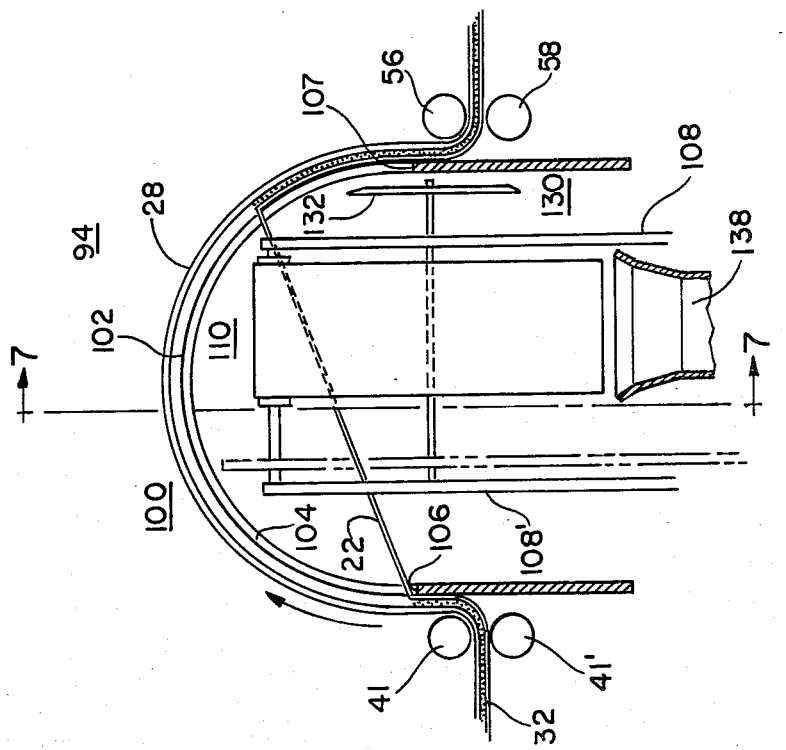
FIG. 6 is a simplified side elevation view of another embodiment of the invention showing only the elastic removal station just prior to the holding of the unattached portion of elastic ribbon by a belt clamping means.
Figure 7:
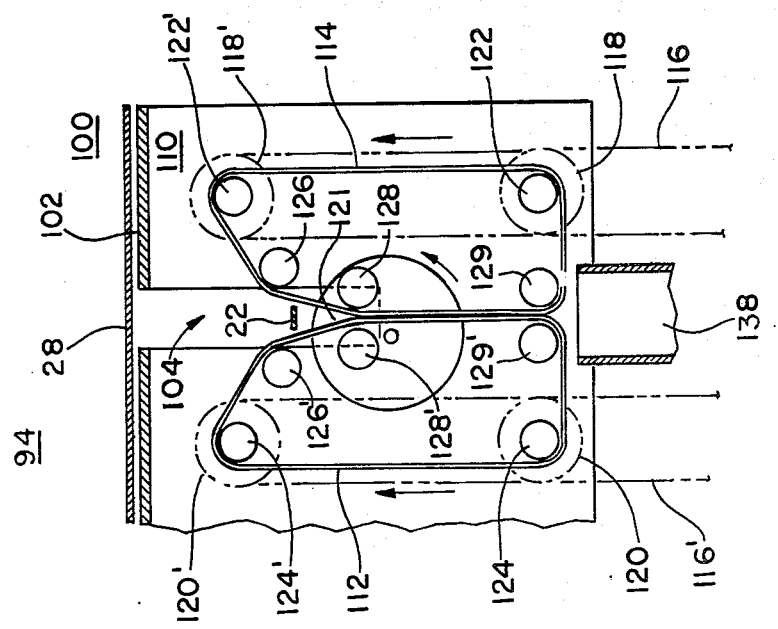
FIG. 7 is a cross-sectional view taken along section line 7—7 of FIG. 6 and showing only the part of the elastic removal station for the clamping of one ribbon.
Figure 8:
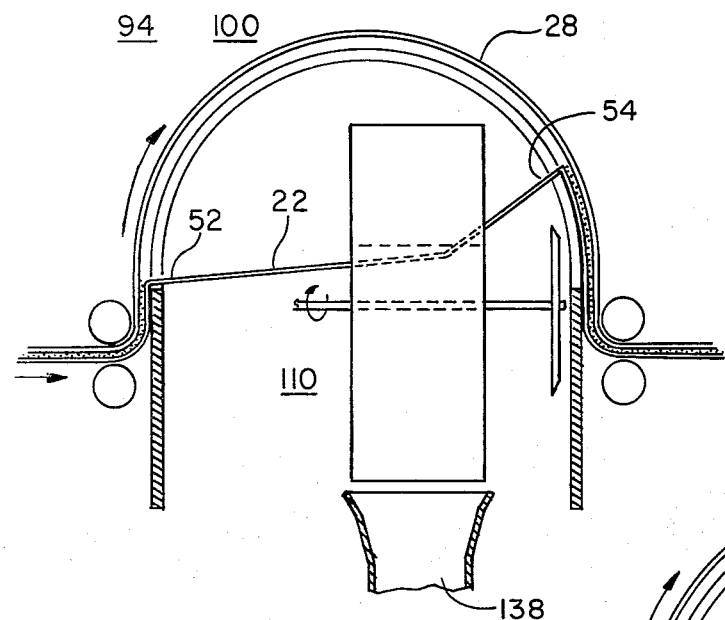
FIG. 8 is a simplified elevation view similar to FIG. 6 showing the unattached portion of elastic ribbon being held clamped and drawn away from the path of the web just prior to the cutting of the leading end of the unattached portion of the elastic ribbon.
Figure 9:
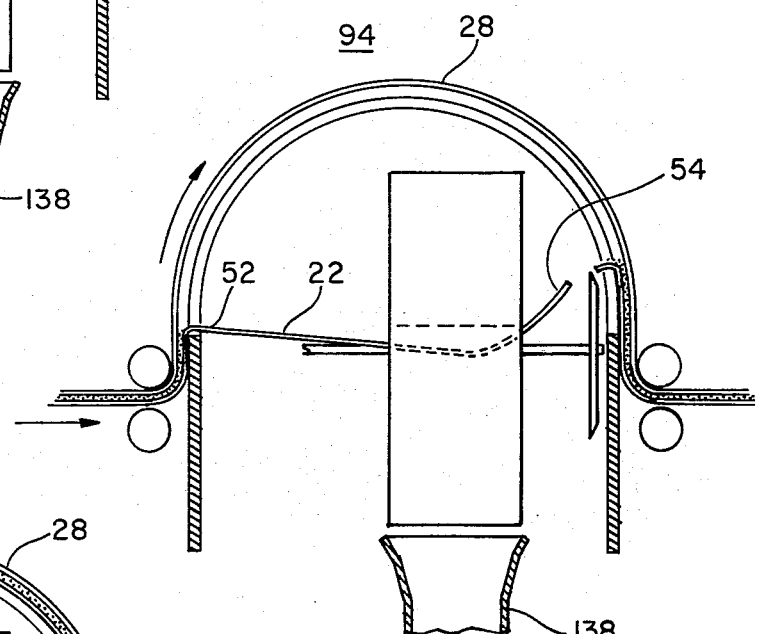
FIG. 9 is a simplified side elevation view similar to FIGS. 6 and 8 showing the unattached portion of tnhe elastic ribbon just subsequent to the cutting of its leading end.
Figure 10:
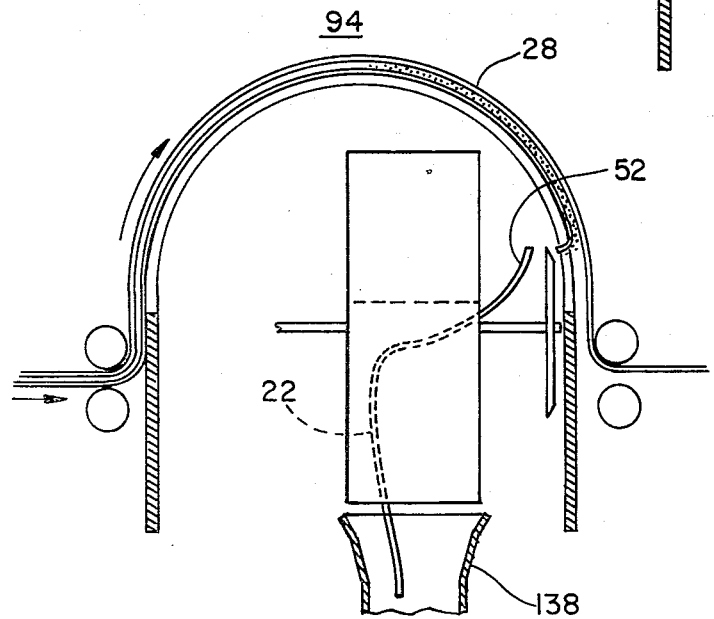
FIG. 10 is a simplified side elevation view similar to FIGS. 6, 8 and 9 showing the unattached portion of the elastic ribbon just subsequent to the cutting of its trailing end.

As the web 28 passes over the surface 102 of support means 100, the unattached ribbon portions 22 will move through the slot 104 and follow a shorter path of movement than that of the web 28 between the ends 106 and 107 of slot 104, as shown in FIGS. 6, 7 and 8. As the leading end 54 of a ribbon portion 22 follows the web 28 toward the slot end 107, the part of the ribbon portion 22 intermediate its ends 52 and 54 will move between the belts 112 and 114 and into the nip 121. The ribbon portion 22 is thus engaged and clamped or held by the clamping means 110 and drawn in a direction away from the path of movement of the web 28 to thereby apply tension to both of the ends 52 and 54 such that upon cutting of the leading end 54, tension will continue to be applied to the trailing end 52 as it moves along the slot 104 toward the cutting blade 132. In FIG. 9, the ribbon portion 22 is shown just subsequent to its having moved into engagement with the cutting blade 132 and its leading end 54 having been severed. In FIG. 10, the trailing end 52 of the ribbon portion 22 is shown just subsequent to being severed from the elastic strip 16 after the trailing end 52 has moved through the slot with the web 28 to the cutting blade 132. Following the severing of the end 52, the cut piece of ribbon portion 22 is moved downward, relative to the view of FIGS. 6–10, by the continuous rotation of the belts 112 and 114 and is dropped from the clamping of the belts into the vacuum removal means 138. The vacuum removal means then removes the cut ribbon piece from the elastic removal station 94.

An apparatus and a method is thus provided for elasticizing only the leg areas of a disposable diaper in which the elastic ribbon that is not needed in the waist area of the diaper is entirely removed. Due to the use of a clamping means which maintains tension on the ends of the elastic ribbon portion that is removed, the cutting of one end does not remove the tension from the second end and thereby prevent the second end from being cut. The apparatus and method are relatively simple so that they can be readily and economically incorporated into a high speed diaper production apparatus.

It will be understood that the foregoing description of the present invention is for purposes of illustration only and that the invention is susceptible to a number of modifications or changes, none of which entail any departure from the spirit and scope of the present invention as defined in the hereto appended claims.

I claim as my invention:

1. In an apparatus for manufacturing elastic leg disposable diapers including means for continuously moving a web of material in the direction of its length and means for attaching portions of a continuously moving elastic ribbon to the web at predetermined spaced apart locations along the length of the web, said predetermined locations corresponding to the leg areas of the finished diapers, the combination comprising:
   means for separating the path of movement of the web and the elastic ribbon between said attached locations;
   means comprising at least two members positioned on opposite sides of the path of movement of the elastic ribbon for clamping the elastic ribbon; and
   means for cutting the unattached portions of the elastic ribbon between said attached locations while the elastic ribbon is separated from the web and clamped by the clamping means.

2. The combination according to claim 1 wherein both the elastic ribbon and the web move between the two members of the clamping means and the clamping means clamps both the ribbon and the web.

3. The combination according to claim 1 wherein:
   the cutting means severs the opposite ends of the unattached portion of the elastic ribbon at different times; and
   the clamping means maintaining tension in the unattached portion of the elastic ribbon subsequent to the first severing of an end to facilitate the second severing of an end.

4. The combination according to claims 1 or 3 wherein the cutting means comprises first and second cutting knives for respectively cutting the leading ends and the trailing ends of the unattached portions of the elastic ribbon.

5. The combination according to claim 1 wherein the two members of the clamping means have facing surfaces moving in the same direction on opposite sides of the elastic ribbon.

6. The combination according to claim 1 wherein the clamping means comprises a pair of belt members having facing surfaces moving in a direction substantially transverse to said path of movement of the elastic ribbon, said facing surfaces engaging each other along a portion of their length, said elastic ribbon moving between the engaged portion of the facing surfaces as the ribbon moves along its path of movement whereby the ribbon is clamped and moved away from its path of movement by the facing surfaces to thereby tension the ribbon during cutting and carry the cut ribbon piece away after cutting.

7. The combination according to claim 1 wherein:
   said separating means includes first and second spaced apart means for separating the path of movement of the web and elastic ribbon;
   said clamping means is positioned between the first and second separating means; and
   the cutting means comprises first and second cutting respectively positioned adjacent the first and second separating means and on opposite sides of the clamping means for cutting the elastic ribbon at two points along the separated and clamped unattached portion of the ribbon.

8. The combination according to claim 7 wherein:
   the two members of the clamping means comprise a pair of rollers; and
   the path of movement of both the web and the ribbon are between the facing surfaces of the rollers.

9. In an apparatus for manufacturing elastic leg disposable diapers including means for continuously moving a web of material in the direction of its length and means for attaching a continuously moving elastic ribbon to the web at predetermined spaced apart locations along the length of the web; said predetermined locations corresponding to the leg areas of the finished diapers, the combination comprising:
   first means for separating the path of movement of the web and the elastic ribbon along a first area between said attached locations;
   second means for separating the path of movement of the web and the elastic ribbon along a second area separate from said first area and between said attached locations;
   means positioned between said two areas for clamping the elastic ribbon; and
   means for cutting both ends of the unattached portions of the elastic ribbon between said attached locations while the ribbon is clamped by the clamping means, one end being cut in one of said areas and the other end being cut in the other of said areas.

10. The combination according to claim 9 wherein:
    the path of movement of the web and the path of movement of the elastic ribbon pass through the clamping means and coincide while so passing through; and
    the clamping means comprises a pair of rotating rollers having a nip through which said paths of movement pass.

11. The combination according to claim 10 wherein the separating means comprises two arcuate shaped spaced apart surface means for guiding the web and the attached portions of the elastic ribbon along a first path, each of the surfaces having a slot through which the unattached portion of the elastic ribbon moves along a second path.

12. In a method for manufacturing elastic leg disposable diapers including continuously moving a web of material and a ribbon of elastic material into engagement with each other and attaching portions of the elastic ribbon to the web along spaced apart locations on the length of the web corresponding to the leg areas of the finished diapers whereby portions of the elastic ribbon are left unattached, the steps comprising:

applying elongating tension to the elastic ribbon;

during the travel of the web and elastic ribbon together, supporting the web along a path of movement that is longer than the path of movement of the unattached portions of the elastic ribbon between the attached spaced apart locations of the web and ribbon whereby said unattached portions of the elastic ribbon are separated from the web along the longer path of movement of the web;

cutting both ends of the unattached separated portions of the elastic ribbon adjacent the portions of the elastic ribbon attached to the web along said spaced apart locations on the web; and holding the web and the unattached portions of the elastic ribbon intermediate the attached portions of the elastic ribbon whereby, when cutting of said ends does not occur simultaneously, the second end cut is maintained under said tension after cutting of the first end.

* * * * *